US009839555B2

(12) United States Patent
de Vries et al.

(10) Patent No.: US 9,839,555 B2
(45) Date of Patent: Dec. 12, 2017

(54) APPLICATOR FOR DELIVERING AN OCCLUDING COMPOUND IN A FALLOPIAN TUBE

(71) Applicant: Urogyn B.V., Nijmegen (NL)

(72) Inventors: Jan Albert de Vries, Zelhem (NL); Ruben Van Der Vleuten, Nijmegen (NL)

(73) Assignee: UROGYN B.V., Nijmegen (NL)

( * ) Notice: Subject to any disclaimer, the term of this patent is extended or adjusted under 35 U.S.C. 154(b) by 0 days.

(21) Appl. No.: 14/396,347

(22) PCT Filed: Apr. 23, 2013

(86) PCT No.: PCT/EP2013/058380
§ 371 (c)(1),
(2) Date: Oct. 22, 2014

(87) PCT Pub. No.: WO2013/160295
PCT Pub. Date: Oct. 31, 2013

(65) Prior Publication Data
US 2015/0114401 A1 Apr. 30, 2015

(30) Foreign Application Priority Data
Apr. 24, 2012 (EP) .................................... 12165366

(51) Int. Cl.
*A61F 6/20* (2006.01)
*A61F 6/00* (2006.01)
(Continued)

(52) U.S. Cl.
CPC ................ *A61F 6/005* (2013.01); *A61F 6/20* (2013.01); *A61F 6/22* (2013.01); *A61B 17/12195* (2013.01)

(58) Field of Classification Search
CPC ... A61F 6/005; A61F 6/22; A61F 6/20; A61B 17/12195
See application file for complete search history.

(56) References Cited

U.S. PATENT DOCUMENTS

| 4,245,623 A | 1/1981 | Erb |
| 5,385,561 A | 1/1995 | Cerny |

(Continued)

FOREIGN PATENT DOCUMENTS

| GB | 2343845 | 5/2000 |
| WO | 9955239 A1 | 11/1999 |

(Continued)

OTHER PUBLICATIONS

International Search Report and Written Opinion dated Sep. 9, 2013 for corresponding International Application No. PCT/EP2013/058380, filed Apr. 23, 2013.

(Continued)

*Primary Examiner* — Tarla Patel
(74) *Attorney, Agent, or Firm* — Steven M. Koehler; Westman, Champlin & Koehler, P.A.

(57) ABSTRACT

Applicator for delivering an occluding compound in a fallopian tube includes a lumen extending between a proximal end connectable to a dispenser for containing uncured occluding compound, and a distal end. A spiral wire with a first end is connected to the distal end of the lumen and a free second end. A disconnecting member is configured to disconnect the spiral wire from the distal end. An actuator is configured to actuate the disconnecting member. The distal end of the lumen can be inserted into the fallopian tube. The spiral wire functions as a guide wire. The curable compound embeds the spiral wire. The actuator can be actuated to disconnect the embedded spiral wire from the distal end of the lumen.

19 Claims, 3 Drawing Sheets

(51) Int. Cl.
*A61F 6/22* (2006.01)
*A61B 17/12* (2006.01)

(56) References Cited

U.S. PATENT DOCUMENTS

| | | | |
|---|---|---|---|
| 5,649,949 A * | 7/1997 | Wallace | A61B 17/12022 600/200 |
| 5,749,894 A | 5/1998 | Engelson | |
| 6,015,424 A | 1/2000 | Rosenbluth et al. | |
| 6,024,754 A | 2/2000 | Engelson | |
| 6,053,860 A | 4/2000 | Brooks | |
| 6,071,230 A | 6/2000 | Henalla | |
| 6,375,669 B1 | 4/2002 | Rosenbluth et al. | |
| 6,572,532 B1 | 6/2003 | Pratt et al. | |
| 8,147,397 B1 | 4/2012 | Witzmann et al. | |
| 8,434,489 B2 * | 5/2013 | Gopal | A61M 25/0067 128/830 |
| 2005/0061329 A1 * | 3/2005 | Tran | A61B 17/12022 128/831 |
| 2005/0187561 A1 | 8/2005 | Lee-Sepsick et al. | |
| 2005/0245876 A1 * | 11/2005 | Khosravi | A61B 17/00491 604/164.1 |
| 2006/0144406 A1 | 7/2006 | Nikolchev et al. | |
| 2007/0000496 A1 | 1/2007 | Nikolchev et al. | |
| 2007/0221230 A1 * | 9/2007 | Thompson | A61B 17/12022 128/207.15 |
| 2007/0261699 A1 * | 11/2007 | Callister | A61F 6/225 128/831 |
| 2008/0004640 A1 * | 1/2008 | Ellingwood | A61B 17/0057 606/151 |
| 2009/0277455 A1 | 11/2009 | Lee-Sepsick et al. | |
| 2011/0313443 A1 * | 12/2011 | Lorenzo | A61B 17/12022 606/200 |
| 2012/0042879 A1 | 2/2012 | Lee-Sepsick et al. | |
| 2013/0220334 A1 | 8/2013 | Lee-Sepsick et al. | |

FOREIGN PATENT DOCUMENTS

| | | |
|---|---|---|
| WO | 2005082299 A2 | 9/2005 |
| WO | 2006088531 A2 | 8/2006 |
| WO | 2007137148 | 11/2007 |
| WO | 2008039807 A2 | 4/2008 |

OTHER PUBLICATIONS

International Search Report and Written Opinion dated Jul. 11, 2013 for International Application No. PCT/EP2013/058486, filed Apr. 24, 2013.
European Office Action dated Aug. 3, 2017 for European Patent Application No. 14195849.6, filed Feb. 12, 2014.

* cited by examiner

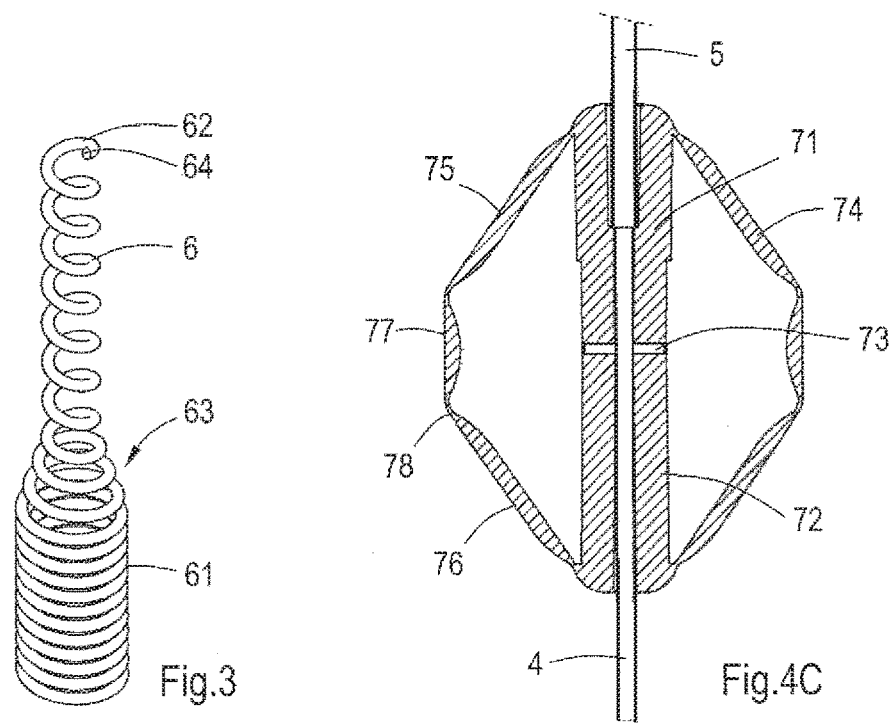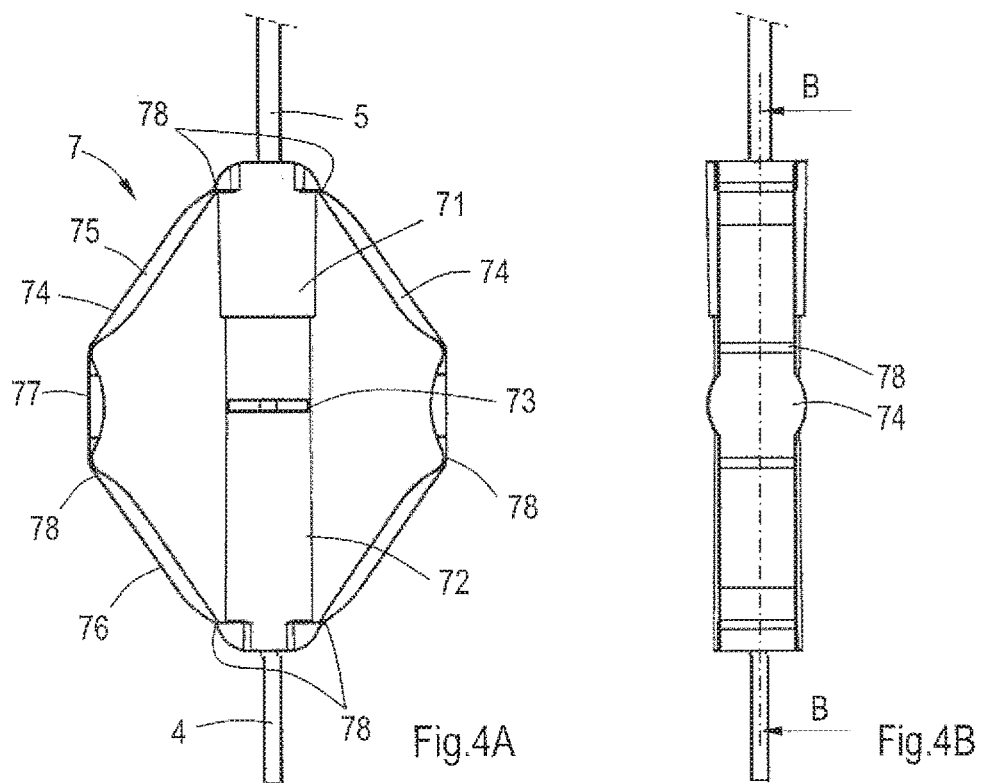

APPLICATOR FOR DELIVERING AN OCCLUDING COMPOUND IN A FALLOPIAN TUBE

CROSS-REFERENCE TO RELATED APPLICATION

The present application is a national stage filing of International patent application Serial No. PCT/EP2013/058380, filed Apr. 23, 2013, and published as WO 2013/160295 in English.

BACKGROUND

The discussion below is merely provided for general background information and is not intended to be used as an aid in determining the scope of the claimed subject matter.

The invention relates to an applicator for delivering a curable occluding compound in a fallopian tube as a contraceptive medium.

An effective method of contraception is to plug the ovarian pathway of a female, for instance by delivering a curing biocompatible polymeric substance into the fallopian tube. After curing, the polymeric substance blocks the fallopian tube preventing egg and sperm cells from joining together.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background. An aspect of the invention provides an applicator for occluding a fallopian tube by an in situ curing compound allowing more accurate positioning of the compound to form a durable and reliable occlusion blocking the ovarian pathway.

An applicator for delivering an occluding compound in a fallopian tube includes:
- a lumen extending between a proximal end connectable to a dispenser for supplying uncured occluding compound, and a distal end;
- a spiral wire with a first end connected to the distal end of the lumen and a free second end;
- a disconnecting member for disconnecting the spiral wire from the distal end; and
- an actuator for actuating the disconnecting member.

In this respect, "distal" refers to the end of the lumen to be inserted into the fallopian tube, while "proximal" refers to the end of the lumen operatively connected or to be connected to a dispensing unit.

The distal end of the lumen, or catheter, with the spiral wire can be inserted into the uterus and the fallopian tube. The spiral wire functions as a guide wire and contributes to accurate targeting and positioning of the lumen into the oviduct. After the spiral wire is introduced into the oviduct a sufficient amount of the curable compound is supplied via the lumen to be delivered into the fallopian tube. The curable compound embeds the spiral wire and cures. After sufficient curing the actuator can be actuated to disconnect the spiral wire from the distal end of the lumen. The lumen is then removed from the uterus leaving behind the plug formed by the spiral wire and the embedding cured polymeric matrix. The plug blocks the fallopian tube to prevent egg cells from being inseminated. The spiral wire enforces the plug and stabilizes the position of the plug in the fallopian tube.

The lumen can be connected to a dispenser of the curable occluding compound, such as a dispenser gun. If the curable compound is a two-component compound, the dispenser may comprise one or more mixing chambers such as a static mixer. The dispenser can for instance be shaped as a gun with a manual actuator or trigger.

In a specific embodiment, the spiral wire is dimensioned in such a way that the first end of the spiral wire snugly fits on the distal end of the lumen. The disconnecting member can for instance be an outer sleeve slideably arranged over the lumen. The sleeve can for example be an outer lumen, forming a double lumen catheter with the inner lumen. The sleeve can be moved towards the distal end to abut the connected end of the spiral wire. Further movement of the outer sleeve will draw the lumen into the sleeve pushing the spiral wire from the distal end of the inner lumen, after the spiral wire has been embedded by the cured polymeric matrix to form the plug.

To improve accurate targeting and positioning the free end of the spiral wire can be dimensioned to have a smaller diameter than the end connected to the distal end of the lumen. Flexibility during positioning can be increased if the free end of the spiral wire has a lower flexural stiffness than the end connected to the distal end of the lumen. This can for example be achieved by providing the free end of the spiral wire with a larger pitch between the windings than the end connected to the lumen. The pitch may for instance gradually increase in the direction of the free end.

To prevent unwanted health effects the spiral wire can be made of a biocompatible material, such as platinum, titanium, gold, silver, nitinol, osmium, stainless steel or mixtures thereof.

Optionally, a material can be used catalyzing the curing reaction of the curable occlusion compound.

The curable occluding compound can for instance be a two-component or multi-component compound which cures after mixing the two or more precursor components. Preferably, the two- or multi-component is curable under the influence of a catalyst. This allows thorough mixing of the precursor components before curing of the compound. Optionally, the spiral wire may contain such a catalyst as a constituent.

A suitable two-component compound may for instance be a silicone elastomer formed from a mixture of two viscous liquid components. The first component can for instance comprise one or more polysiloxanes, while the second component may comprise one or more suitable cross linking agents, optionally pre-mixed with one or more polysiloxanes.

Examples of suitable polysiloxanes include poly (dimethyl) siloxane, such as trimethylsiloxy terminated polydimethyl siloxane, and vinyldimethyl terminated dimethyl polysiloxane.

Examples of suitable cross-linking agents include trimethyl methyl-hydrodimethyl siloxane, propyl ortho silicate and mixtures thereof, although any suitable alternative cross-linking agent(s) may also be used.

The polysiloxanes may be reinforced with an additive such as amorphous silica. To prepare the occluding compound the components can be mixed, e.g., in equal parts or in any suitable ratio. The components can for instance be mixed just prior to injection into the lumen of the applicator to form a flowable, viscous composition, which is then injected into the fallopian tube where it cures in situ to a rubbery consistency. Examples of suitable catalysts include platinum (Pt) catalysts. The polysiloxane components can polymerize in situ in about 3-15 minutes at body temperature. The resulting matrix is biocompatible and is not absorbed into the body.

In a specific embodiment of the applicator the actuator may comprise a first section connected to a proximal end of the sleeve and a second section connected to a proximal section of the lumen. The first and second sections can be moved relative to each other in a direction parallel to a longitudinal direction of the lumen. Optionally, the first and second sections of the actuator are connected by a seal breakable by moving the two sections apart. This way, a pre-determined force needs to be overcome before the actuator can move the sleeve relative to the lumen and the risk of unintentional actuation is substantially reduced.

In a refinement, the first and second sections of the actuator are bridged by a squeezer with a first end hingeably connected to the first section of the actuator, and a second end hingeably connected to the second section of the actuator. This way, a simple and easy squeeze movement is sufficient to actuate the actuator. Optionally, the squeezer comprises a middle section hingeably connected to the first and second end of the squeezer. Such a middle section provides an area of engagement for an appropriate squeeze movement. Preferably, the actuator comprises two oppositely arranged squeezers.

The disclosed actuator can be used with any type of double lumen catheter, comprising an inner lumen and an outer lumen slideably encasing the inner lumen, with or without a spiral wire as disclosed above.

BRIEF DESCRIPTION OF THE DRAWINGS

Aspects of the invention will be further explained under reference to the accompanying drawings, in which:

FIG. 3 shows in side view a spiral wire of the applicator of FIG. 1;
FIGS. 4A-C show a front view, side view and cross section respectively of an actuator of the applicator of FIG. 1.

DETAILED DESCRIPTION OF THE ILLUSTRATIVE EMBODIMENTS

Figure 1:
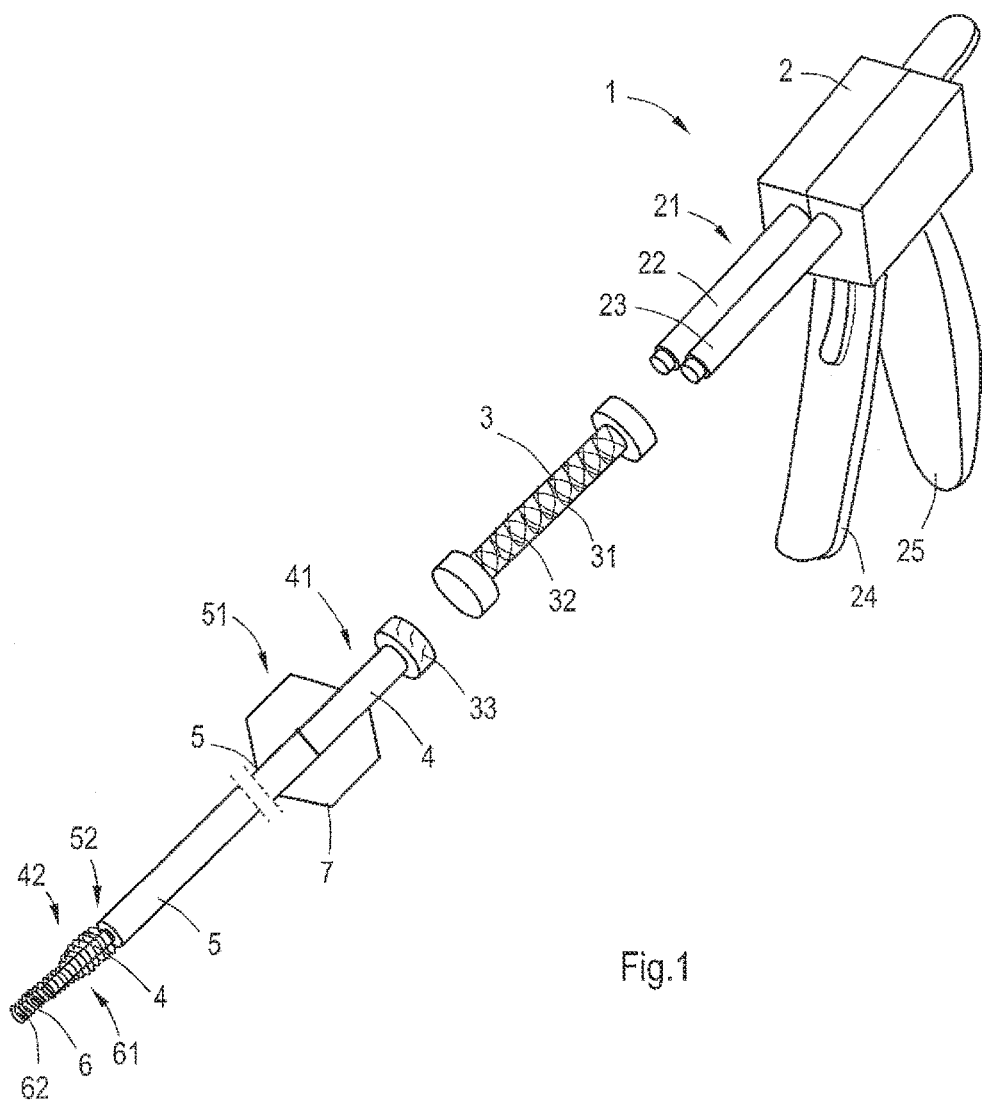
FIG. 1 shows an exemplary embodiment of an applicator.

FIG. 1 shows an applicator 1 comprising a dispenser 2, a static mixer 3, a flexible lumen 4 encased in a flexible outer sleeve or outer lumen 5, and a spiral wire 6 with one end attached to the lumen 4.

The dispenser 2 comprises a pre-filled cartridge 21 containing two side-by-side, pre-filled chambers 22 and 23, both comprising a liquid precursor component of the curable occluding compound. The respective precursor components are kept separate within the chambers 22, 23 until the compound is delivered to the targeted area of a patients' fallopian tube. In the shown exemplary embodiment the two chambers 22, 23 are of equal volume and a plunger (not shown) is used to apply pressure to each chamber through application of a squeezing force applied by hand to a trigger 24 and a handle 25 at the lower section of the dispenser 2. As pressure is applied part of the contents of the two chambers 22, 23 is pushed into and through the static mixer 3 and mixed together to form a liquid composition for injection into a fallopian tube.

In this exemplary embodiment the static mixer 3 has a static helical element 31 disposed in a cavity 32 inside the static mixer 3. Other suitable mixing elements may also be used, if so desired.

The lumen 4 comprises a proximal end 41 attached to the end of the static mixer 3 by luer-lock adapters 33. These luer-lock adapters 33 can for instance have a high-flow, wide inner-diameter and low pressure fittings that provide improved flow of the material with reduced back pressure on the system to lessen the squeezing pressure exerted by the user on the trigger 24 and handle 25.

The spiral wire 6 comprises one end 61 placed on a distal end 42 of the lumen 4, and a free end 62. The diameter of the windings at the free end 62 are smaller than the diameters of the windings at the end connected to the lumen 4. The pitch between the windings at the free end 62 is larger than the pitch between the windings at the other end 61. As a result, the flexural stiffness of the spiral wire 6 is less at its free end 62, so the free end 62 can effectively be used as a guide wire when the lumen 4 with the spiral wire 6 is moved to the targeted position within the fallopian tube. The free end 62 comprises an inwardly bent tip 64 to prevent perforation of the wall of the fallopian duct.

The outer sleeve 5 and the lumen 4 are coaxial and are slideable relative to each other. The sleeve 5 has a distal end 52 abutting the spiral wire 6. An actuator 7 connects the proximal end 41 of the lumen 4 with the proximal end 51 of the outer sleeve 5. The actuator 7 is described in more detail with reference to FIG. 4. By squeezing the actuator 7 the outer sleeve 5 is pushed against the spiral wire 6 and removes the spiral wire 6 from the distal end 42 of the lumen 4.

Figure 2A:
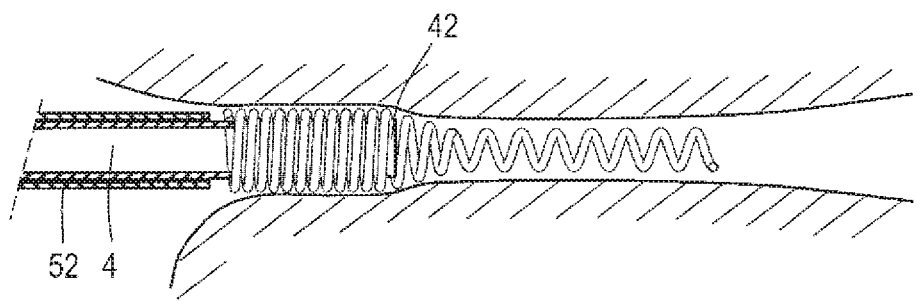
FIG. 2A-D show in cross section consecutive steps of use of the applicator of FIG. 1.
Figure 2B:
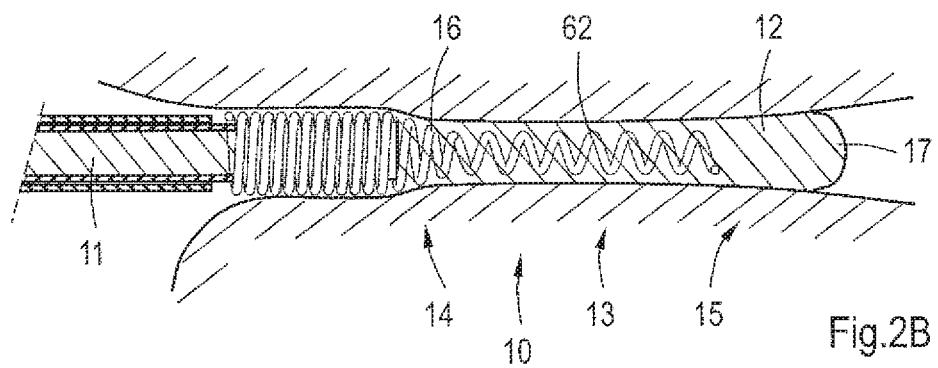

In FIG. 2A the distal end 42 of the lumen 4 with the spiral wire 6 is introduced into a fallopian tube 10. The distal end 52 of the outer sleeve 5 is close to the end of the spiral wire 6 fitting over the distal end of the lumen 4. After accurate positioning of the spiral wire 6 the trigger 24 of the dispenser 2 is actuated and a sufficient amount of the components of the curable occlusion compound 11 is forced to flow via the static mixer 2 static mixer 3 and lumen 4 into the targeted section of the fallopian tube 10, as shown in FIG. 2B. The mixed components cure to form a plug 12 embedding the free end 62 of the spiral wire 6. The compound 11 is delivered to a part of the fallopian tube 10 with a narrow section 13 and widening end sides 14, 15. The plug 11 copies local geometry of the fallopian tube 10 and has wider end parts 16, 17 at both sides which cannot pass the narrow section 13.

To promote curing speed, the spiral wire may contain a catalyst, such as platinum. The curable compound cures in about 2-15 minutes, e.g. in about 2-6 minutes at body temperature.

Figure 2C:
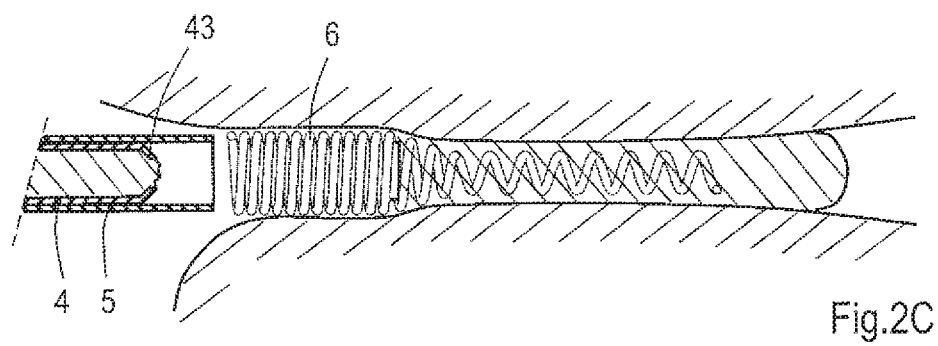
Figure 2D:
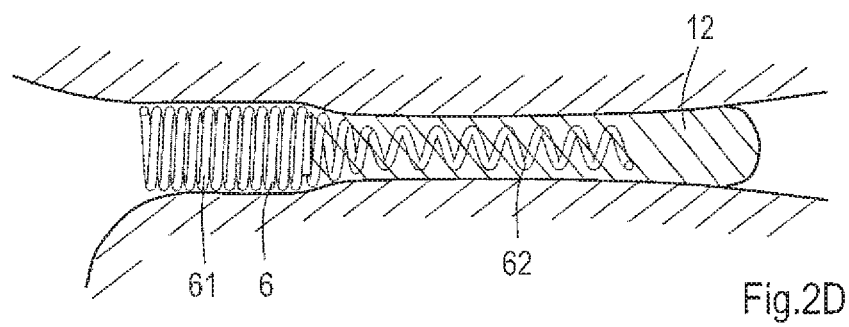

At the proximal end of the lumen 4 and the outer sleeve 5, the user can actuate the actuator 7 to retract the lumen 4, while the outer sleeve 5 remains in place. The outer sleeve 5 abuts the spiral wire 6 and prevents that the wire 6 moves with the lumen 4. As a result the lumen 4 is separated from the spiral wire 6 (see FIG. 2C). The distal end 42 of the lumen 4 comprises a narrowed discharge opening 43 to achieve that the occlusion compound 11 left behind in the lumen 4 breaks free from the plug 12 at the position of the distal end 42. The lumen 4 and the outer sleeve 5 can now be removed from the patient, leaving the cured plug 12 with the spiral wire 6 behind, as shown in FIG. 2D. The large diameter end 61 of the spiral wire 6 extends from one end of the plug 12 in the direction of the uterus. This end 61 could also be embedded in the cured material and encloses a tail of cured plug material.

FIG. 3 shows the spiral wire 6 as a separate part. The wire diameter can for instance be about 0.1-0.50 mm, e.g., about 0.2 mm. The length of the spiral wire will typically range between 7-13 mm, e.g., between 10-12 mm, such as between 10.5-11.5 mm. The large diameter end 61 which is to be attached to a distal end 42 of a lumen 4, will typically have a length of about 2-6 mm, e.g., about 3-5 mm, such as about 3.3-3.9 mm, and an inner diameter of about 1-2 mm, e.g., about 1.5 mm. The free end 62 of the spiral wire 6 can for instance have a length of about 4-8 mm, e.g., of about 5.5-6.5 mm and an inner diameter of about 0.4-0.80 mm, e.g., about 0.6 mm. The pitch can be used to adjust flexural stiffness of the free end 62. If the stiffness of the free end 62 is less, usability of the free end 62 as a guide wire will be improved. The pitch between the windings of the spiral wire 6 at its free end 62 can for example be about 0.6-1.20 mm, such as about 0.7-0.90 mm. Optionally, the pitch of the free end 62 gradually increases in the direction away from the other end 61. In the exemplary embodiment of FIG. 3 the spiral wire 6 comprises a transitional section 63 between the free end 62 and the opposite end 61. The transitional section 63 tapers from the diameter of the end 61 to the smaller diameter of the free end 62. The length of the transitional section 63 can for instance be about 1-2 mm, e.g. about 1.5 mm. Optionally, the material of the spiral wire 6 may contain copper or a similar spermicidal compound to enhance the contraceptive effectiveness of the occlusion.

FIGS. 4A-C show the actuator 7 in front view, side view and cross section, respectively. The actuator 7 comprises a first tubular section 71 connected to a proximal end of the sleeve 5 and a second tubular section 72 connected to a proximal section of the lumen 4. The first and second tubular sections 71, 72 are connected by a seal 73 which is broken if the two tubular sections 71, 72 are forced to move away from each other by a given minimum tensile force. This seal 73 helps to avoid unintentional withdrawal of the inner lumen 4.

The first and second tubular sections 71, 72 of the actuator 7 are bridged by two oppositely arranged squeezers 74 with a first end 75 hingeably connected to the first section 71 of the actuator 7, and a second end 76 hingeably connected to the second section 72 of the actuator 7. A middle section 77 hingeably bridges the first and second ends 75, 76 of the squeezer 74. The respective hingeable connections are constructed as integral film hinges 78. A user can squeeze the middle sections 77 of the two opposite squeezers 74 together. As a result, the squeezers 74 will transfer a tensile force to the first and section tubular sections 71, 72 of the actuator 7. If the tensile force exceeds a given limit, the seal 73 will break and the first and second tubular sections 71, 72 are moved apart. Since the first and second tubular sections 71, 72 are connected to the lumen 4 and the outer sleeve 5 respectively, the outer sleeve 5 is moved over the lumen 4 until its distal end 52 abuts the spiral wire 6. Continuation of the actuation force will withdraw the lumen 4 into the outer sleeve 5 and separate the spiral wire 6 from the distal end 42 of the lumen 4.

The invention claimed is:

1. An applicator comprising:
   a dispenser;
   a lumen extending between a distal end and a proximal end, the proximal end being configured to connect to the dispenser to receive fluidic curable occluding compound from the dispenser, the lumen being configured to guide flow of the fluidic curable occluding compound down the lumen, and discharge the fluidic curable occluding compound at the distal end through a discharge opening;
   a wire with a first end connected to the distal end of the lumen and a free second end, wherein the wire is positioned to engage the fluidic curable occluding compound discharged at the distal end of the lumen;
   a disconnecting structure on the distal end of the lumen and abutting said first end of the wire; and
   an actuator connected to the disconnecting structure and configured to actuate the disconnecting structure to completely disconnect the wire having the fluidic curable occluding compound from the lumen.

2. The applicator according to claim 1 wherein the first end of the wire snugly fits on the distal end of the lumen and wherein the disconnecting structure is an outer sleeve slideably arranged over the lumen.

3. The applicator according to claim 2 wherein the actuator comprises a first section connected to a proximal end of the outer sleeve and a second section connected to a proximal section of the lumen, wherein the first and second sections being movable relative to each other in a direction parallel to a longitudinal direction of the lumen.

4. The applicator according to claim 3 wherein the first and second sections of the actuator are connected by a seal breakable by moving the first and second sections apart.

5. The applicator according to claim 3 wherein the first and second sections of the actuator are bridged by a squeezer with a first end hingeably connected to the first section of the actuator, and a second end hingeably connected to the second section of the actuator.

6. The applicator according to claim 5 wherein the squeezer comprises a middle section hingeably connected to the first and second end of the squeezer.

7. The applicator according to claim 5 wherein the actuator comprises two oppositely arranged squeezers.

8. The applicator according to claim 1 wherein the free second end of the wire has a smaller diameter than the first end connected to the distal end of the lumen.

9. The applicator according to claim 1 wherein the free second end of the wire has a lower flexural stiffness than the first end connected to the distal end of the lumen.

10. The applicator according to claim 9 wherein the free second end of the wire comprises windings with a larger pitch than the first end connected to the distal end of the lumen.

11. The applicator according to claim 10 wherein a pitch gradually increases in a direction of the free second end.

12. The applicator according to claim 1 wherein the wire comprises a constituent catalyzing curing of the fluidic curable occluding compound.

13. The applicator according to claim 1 wherein the applicator comprises the dispenser operatively connected to the proximal end of the lumen via a static mixer.

14. The applicator according to claim 1 wherein the wire is a spiral wire.

15. A method comprising:
   providing a detachable receiving member connected to a distal end of a lumen;
   providing a fluidic curable occluding compound through a discharge opening at the distal end of the lumen and in the detachable receiving member, wherein the fluidic curable occluding compound discharged at the distal end of the lumen engages the detachable receiving member;

moving a disconnecting member towards the distal end of the lumen or the distal end of the lumen towards the disconnecting member, such that a proximal end of the detachable receiving member abuts the disconnecting member; and applying a force between the disconnecting member and the proximal end of the detachable receiving member to completely remove the detachable receiving member having the fluidic curable occluding compound from the distal end of the lumen, wherein the fluidic curable occluding compound cures subsequent to being received by the detachable receiving member.

16. The method according to claim 15 wherein the detachable receiving member is a wire.

17. The method according to claim 16 wherein the wire is a spiral wire.

18. The method according to claim 15 wherein the disconnecting member is a sleeve slideably arranged over the lumen, and wherein the applying of the force between the disconnecting member and the proximal end of the detachable receiving member includes pushing the detachable receiving member from the distal end of the lumen to remove the detachable receiving member.

19. An applicator comprising:

a fluidic curable occluding compound;

a lumen extending between a proximal end and a distal end, the proximal end configured to receive the fluidic curable occluding compound and guide flow of the fluidic curable occluding compound down the lumen towards a discharge opening at the distal end;

a wire with a first end connected to the distal end of the lumen and a free second end, wherein the wire is positioned to engage the fluidic curable occluding compound discharged at the distal end of the lumen;

a disconnecting member abutting said first end of the wire; and an actuator connected to the disconnecting member and configured to apply a force between the disconnecting member and the first end of the wire to completely remove the wire from the distal end of the lumen and separate fluidic curable occluding compound with the wire from fluidic curable occluding compound in the lumen.

* * * * *